US005733550A

United States Patent [19]

Rock

[11] Patent Number: 5,733,550
[45] Date of Patent: Mar. 31, 1998

[54] METHOD FOR ENHANCING THE ASSOCIATION OF EXOGENOUS PEPTIDES WITH CLASS I MHC MOLECULES ON THE SURFACE OF ANTIGEN PRESENTING CELLS WITH β-MICROGLOBULIN

[75] Inventor: Kenneth L. Rock, Chestnut Hill, Mass.

[73] Assignee: Dana-Farber Cancer Institute, Inc., Boston, Mass.

[21] Appl. No.: 461,213

[22] Filed: Jun. 5, 1995

Related U.S. Application Data

[63] Continuation of Ser. No. 207,910, Mar. 7, 1994, abandoned, which is a continuation of Ser. No. 918,224, Jul. 21, 1992, abandoned, which is a continuation-in-part of Ser. No. 857,698, Mar. 25, 1992, abandoned, which is a continuation of Ser. No. 521,576, May 10, 1990, abandoned.

[51] Int. Cl.$^6$ ............... A61K 39/00; A01N 63/00; C07K 1/00; C07K 14/00
[52] U.S. Cl. ............... 424/185.1; 424/184.1; 424/93.71; 530/350; 530/351
[58] Field of Search ............... 424/185.1, 184.1, 424/93.71

[56] References Cited

FOREIGN PATENT DOCUMENTS

WO 79/00160  4/1979  WIPO .
WO 80/01986  10/1980  WIPO .

OTHER PUBLICATIONS

Anderson et al, Studies on the Cytophilic Properties of Human $\beta_2$ Microglobulin, *The Journal of Immunology*, vol. 114: 997–1000 (Mar. 1975).
Bernabeu et al, $\beta_2$–Microglobulin from serum associates with MHC class I antigens on the surface of cultured cells, *Nature*, vol. 308: 642–645 (Apr. 12, 1984).
Bevan, Michael J., Class discrimination in the world of immunology, *Nature*, vol. 325: 192–194 (Jan. 15, 1987).
Bevan, Michael J., Stimulating killer cells, *Nature*, vol. 342: 478–479, (Nov. 30, 1989).
Braciale et al, Antigen Presentation Pathways to Class I and Class II MHC–Restricted T Lymphocytes, *Immunological Reviews*, No. 98: 95–114 (1987).
Carbone et al, Induction of Cytotoxic T Lymphocytes by Primary In Vitro Stimulation With Peptides, *J. Exp. Med.*, vol. 167: 1767–1779, (Jun., 1988).
Carbone and Bevan, Induction of Ovalbumin–Specific Cytotoxic T Cells By In Vivo Peptide Immunization, *J. Exp. Med.*, vol. 169: 603–612, (Mar. 1989).
Deres et al, In vivo priming of virus–specific cytotoxic T lymphocytes with synthetic lipopeptide vaccine, *Nature*, vol. 342: 561–564 (Nov. 30, 1989).
Germain, Ronald N., The ins and outs of antigen processing and presentation, *Nature*, vol. 322: 687 (Aug. 1986).
Hyafil and Strominger, Dissociation and exchange of the $\beta_2$–microglobulin subunit of HLA–A and HLA–B antigens, *Proc. Natl. Acad. Sci. USA*, vol. 76: 5834–5838 (Nov. 1979).

Kefford et al, Serum $\beta_2$–microglobulin binds to a T–cell differentiation antigen and increases its expressing, *Nature*, vol. 308: 641–642 (Apr. 12, 1984).
Maryanski et al, H–2–restricted cytolytic T cells specific for HLA can recognize a synthetic HLA peptide, *Nature*, vol. 324: 578–579 (Dec. 11, 1986).
Moore et al, Introduction of Soluble Protein into the Class I Pathway of Antigen Processing and Presentation, *Cell*, vol. 54: 777–785 (Sep. 9, 1988).
Perkins et al, Identical Peptides Recognized By MHC Class I–and II–Restricted T Cells, *J. Exp. Med.*, vol. 170: 279–289 (Jul. 1989).
Tevethia et al, Biology of Simian Virus 40 (SV40) Transplantation Antigen (TrAg), *Virology*, vol. 107: 13–23 (1980).
Townsend et al, Association of class I major histocompatibility heavy and light chains induced by viral peptides, *Nature*, vol. 340: 443–448 (Aug. 10, 1989).
Townsend et al, Cytotoxic T Cells Recognize Fragments of the Influenza Nucleoprotein, *Cell*, vol. 42: 457–467 (Sep. 1985).
Townsend et al, The Epitopes of Influenza Nucleoprotein Recognized by Cytotoxic T Lymphocytes Can Be Defined with Short Synthetic Peptides, *Cell*, vol. 44: 959–968 (Mar. 28, 1986).
Watari et al, A Synthetic Peptide Induces Long–Term Protection From Lethal Infection With Herpes Simplex Virus 2, *J. Exp. Med.*, vol. 165: 459–470 (Feb. 1987).
Wraith and Askonas, Induction of Influenza A Virus Cross–reactive Cytotoxic T Cells by a Nucleoprotein/Hemagglutinin Preparation, *J. Gen. Virol.*, vol. 66: 1327–1331 (1985).
Yamada et al, Influenza Virus Hemagglutinin–Specific Cytotoxic T Cell Response Induced By Polypeptide Produced in *Escherichi coli*, *J. Exp. Med.*, vol. 162: 663–674 (Aug. 1985).
Yawdell et al, Cells process exogenous proteins for recognition by cytotoxic T lymphocytes, *Science*, vol. 239: 637–40 (1988).

(List continued on next page.)

*Primary Examiner*—Lynette F. Smith
*Attorney, Agent, or Firm*—Julia D. Hart

[57] ABSTRACT

The present invention provides a method for enhancing the association of exogenous peptides with class I MHC molecules on the surface of antigen presenting cells to thereby sensitize the target cells for class I MHC-restricted cytotoxic T cell response. The method involves obtaining the peptides of interest and presenting the peptides to the appropriate antigen presenting cells in the presence of an elevated level of free $\beta_2$-microglobulin.

The method of the present invention can also be used to prime naive populations of T lymphocytes for antigen-specific class I MHC-restricted cytotoxic T cell response with exogenous peptide and is useful in both in vitro and in vivo applications. A new use for purified $\beta_2$-microglobulin as an adjuvant for synthetic peptide vaccines is also provided.

22 Claims, 9 Drawing Sheets

OTHER PUBLICATIONS

Kefford et al, Serum $\beta_2$-M binds to a T-cell differentiation antigen and increases its expression, *Nature*, vol. 308: 641–642 (1984).

Rock et al, Reassociation with beta 2-microglobulin is necessary for Kb class I major histocompatibility complex binding of exogenous peptides 87(19):7517–7521 (Oct., 1990).

Rock et al, Reassociation with β-microglobulin is necessary for $D_b$ class I major hisotcompatibility complex binding of an exogenous influenza peptide, *Proc. Natl. Acad. Sci. USA*, vol. 88: 301–304 (1991).

Vitiello et al, The Role of $\beta_2$-Microglobulin in Peptide Binding by Class I Molecules, *Science*, vol. 250: 1423–1426 (Dec. 1990).

Koslowski et al, Excess $\beta_2$ microglobulin promoting functional peptide association with purified soluble class I MHC molecules, *Nature*, vol. 349: 74–77 (Jan. 1991).

Chen & Parham, Direct binding of influenza peptides to class I HLA molecules, *Nature*, vol. 337: 743–745 (Feb. 23, 1989).

Benjamin et al, Peptide binding to empty HLA-B27 molecules of viable human cells, *Nature*, vol. 351: 74–77 (May 2, 1991).

Luescher et al, Specific binding of antigenic peptides to cell-associated MHC class I molecules, *Nature*, vol. 351: 72–74 (May 2, 1991).

Luescher et al, Interaction Of Antigenic Peptides with MHC Class I Molecules on Living Cells Studied by Photoaffinity Labeling, *Journal of Immunology*, vol. 148: 1003–1011 No. 4., (Feb. 15, 1992).

Bjorkman et al, The foreign antigen binding site and T cell recognition regions of class I histocompatibility antigens, *Nature*, vol. 329: 512–518 (Oct. 8, 1987).

Bastin et al, Use of Synthetic Peptides of Influenza Nucleoprotein to Define Epitopes Recognized by Class I-Restricted Cytotoxic T Lymphocytes, *J. Exp. Med.*, vol. 165: 1508–1521 (Jun. 1987).

Maryanski et al, Synthetic Peptides As Antigens and Competitors in Recognition by H–2–Restricted Cytolytic T Cells Specific For HLA, *J. Exp. Med.*, vol. 167: 1391–1405 (Apr. 1988).

Yewdell and Bennink, The Binary Logic of Antigen Processing and Presentation to T Cells, *Cell*, vol. 62: 203–206 (Jul. 27, 1990).

Schumacher et al, Direct Binding of Peptide to Empty MHC Class I Molecules on Intact Cells and In Vitro, *Cell*, vol. 62: 563–567 (Aug. 10, 1990).

Yewdell and Bennink, Brefeldin A Specifically Inhibits Presentation of Protein Antigens to Cytotoxic T Lymphocytes, *Science*, vol. 244: 1072–1075 (Jun. 2, 1989).

Braciale et al, Antigen Presentation Pathways to Class I and Class II MHC–Restricted T, *Immunological Reviews*, No. 98: 104–108 (1987).

METHOD FOR ENHANCING THE ASSOCIATION OF EXOGENOUS PEPTIDES WITH CLASS I MHC MOLECULES ON THE SURFACE OF ANTIGEN PRESENTING CELLS WITH β-MICROGLOBULIN

STATEMENT OF RELATED APPLICATIONS

This application is a continuation of application Ser. No. 08/207,910, filed Mar. 7, 1994, now abandoned, which is a continuation of application Ser. No. 07/918,224 filed on Jul. 21, 1992 (now abandoned) which is a continuation-in-part of my prior application U.S. Ser. No. 07/857,698 filed on Mar. 25, 1992, now abandoned which in turn is a continuation of U.S. Ser. No. 07/521,576, filed on May 10, 1990, now abandoned.

GOVERNMENT RIGHTS IN INVENTION

This invention was made with the support of Government Grants AI 20248 and CA 46967 from the National Institutes of Health. The government of the United States of America has certain rights in this invention.

TECHNICAL FIELD OF INVENTION

The present invention relates to a method for enhancing the association of exogenous peptides with class I MHC molecules on the surface of antigen presenting cells of the immune system, to the induction of a cytotoxic T lymphocyte response to exogenous peptides in a mammalian host, and to the extension of this methodology to vaccination with synthetic peptides to prime for cytotoxic T lymphocyte response.

BACKGROUND OF THE INVENTION

Vaccines have long been utilized by man to aid in the prevention of infectious diseases in both humans and animals. Active immunization procedures have more recently been tested in other areas, such as the prevention and treatment of malignant disorders. The use of vaccines is based upon the stimulation of the specific immune response, which includes both humoral and cellular components. Although vaccination is often considered in terms of its ability to stimulate antigen-specific antibody, vaccine effectiveness is not necessarily determined by the induction of serum antibody alone (humoral factors). Rather it is determined by the demonstration of enhanced protection against disease, which may include cytotoxic T lymphocyte response. Cytotoxic T lymphocytes provide an effective defense against many intracellular pathogens. In some cases, full protection can be achieved even in the absence of an antibody response.

Historically, vaccines have been prepared by killing or attenuating pathogenic organisms, e.g. viruses, and then injecting the resulting virus particles into a patient or host mammal. One significant disadvantage of such vaccines is that they always involve an inherent threat that the virus is not sufficiently attenuated or killed. There is thus the potential for the vaccine to cause the disease against which protection is sought. Another limitation of this approach is that most pathogens, when killed, do not effectively stimulate cytotoxic T lymphocyte immunity.

The threat of morbidity from unattenuated pathogens can usually be overcome by using a specific component of the pathogen as the immunogen. The component used is typically a protein from, for example, a viral capsid or envelope which forms an outer portion of the virus. As with the attenuated vaccines, this approach is limited because most protein antigens that are introduced into the extracellular fluid do not effectively stimulate cytotoxic T lymphocyte immunity.

More recently, certain pathogen-related proteins have been immunologically mimicked with synthetic peptides whose amino acid sequence corresponds to that of an antigenic determinant domain of the pathogen-related protein. For example, U.S. Pat. No. 4,974,168 describes leukemia associated immunogens that are relatively short peptide sequences corresponding to the antigenic determinant domains of a leukemia associated virus envelope protein. Similarly, other peptide immunogens have been reported by Sutcliffe et al, *Nature*, Vol. 287, pp. 801–805 (1980); Lerner et al, *Proc. Natl. Acad. Sci. U.S.A.*, Vol. 78, pp. 347–47 (1981) and Bittle et al, *Nature*, Vol. 298, pp. 30–33 (1982). Peptide vaccines based upon such immunogens are expected to be safe and highly specific. The peptide sequence of a natural protein can be determined either from the protein itself or from the nucleotide sequence of the gene encoding the protein.

Research with synthetic peptides has demonstrated that peptide immunization can stimulate class II MHC-restricted helper T lymphocytes in a host. Helper T cells are a critical component of the host immune response, since they augment the activities of other immune system cells, including the antibody-secreting B lymphocytes. It has also been shown that peptides can sensitize target cells in vitro, which raised the possibility that cytotoxic T lymphocyte immunity might also be initiated upon immunization with synthetic peptides. However, most attempts at inducing a cytotoxic T lymphocyte response in vivo have failed, and those that have met with success are often unreproducible. The general inability of synthetic peptides to prime cytotoxic T lymphocytes in vivo presents a formidable hurdle to their effective use in vaccination.

The reason for the inability of synthetic peptides to consistently prime class I MHC-restricted T cells in vivo was not known prior to the present invention. The form in which antigen interacts with and is displayed by both class I and class II MHC molecules on the cell surface is thought to be as a small peptide. Thus, it was logically expected that small peptides in the extracellular fluid might bind to class I MHC molecules on the cell surface, bypassing intracellular processes, and be presented to the immune system. This apparently does occur in vitro. As one of many examples, Maryanski et al. demonstrated that certain peptides can sensitize class I MHC antigen presenting cells for lytic action by antigen-specific cytotoxic T lymphocytes at high doses of exogenous peptides in vitro. *Nature*, Vol. 324, No. 11 (1986). See also, Townsend et al, *Cell*, Vol. 44, pp. 959–68 (March 1986).

Peptide fragments at high concentrations can also prime naive populations of lymphocytes for cytotoxic T cell response in culture. Carbone et al, *J. Exp. Med.*, Vol. 167, pp. 1767–79 (June 1988). Although it is unclear why in vitro priming has been successful, there is some suggestion that the high concentrations of peptides typically employed in in vitro cultures may allow intracellular complexes to form or may drive the association of peptides directly with unoccupied class I molecules on the cell surface.

Despite the observations regarding in vitro sensitization and priming for CTL response, the events generally do not occur in vivo in a manner that has allowed stimulation of cytotoxic T lymphocyte response. One possible explanation is that the concentration of circulating peptides is not maintained at a high enough level for this type of presentation to be effective in vivo. Even if sufficiently high concentrations of synthetic peptide could be maintained in a host organism to initiate CTL response, the cost of using such high concentrations of peptides with present technology would be prohibitive. Synthetic peptides are extremely expensive and vaccines requiring high concentrations of peptide would be unattractive for these reasons. More recent evidence, which is the subject of my prior patent applications, suggests that free $\beta_2$-microglobulin can be used to promote the association of exogenous peptides to associate with class I MHC molecules on the surface of antigen presenting cells.

It is an object of the present invention to provide a method for enhancing the association of exogenous peptides with class I MHC molecules on the surface of antigen presenting cells.

Another object of the present invention is to provide a method for priming class I MHC-restricted cytotoxic T cell response with peptides.

Yet another object of the present invention is to provide a method for priming cytotoxic T cell response in vivo with peptides.

A still further object of the present invention is to provide an adjuvant that can be used with synthetic peptide vaccines to enhance the immunogenicity of pathogen-related peptides.

SUMMARY OF THE INVENTION

These as well as other objects and advantages are accomplished by the present invention, which provides a method for priming a cytotoxic T lymphocyte response to exogenous peptides in a mammalian host in vivo. The method involves: (a) obtaining the exogenous peptides of interest and (b) sensitizing host cells, comprising antigen-presenting cells bearing class I MHC molecules, to the peptides in the presence of free $\beta_2$-microglobulin and exposing the sensitized cells to a population of the host's T lymphocytes, wherein the $\beta_2$-microglobulin is present in an amount greater than that normally present in the extracellular fluid of a mammal of the same species as the host and sufficient to stimulate an immune response to the exogenous peptide. In a particularly preferred embodiment, the class I peptides comprise at least one pathogen-related peptide. The host's antigen presenting cells can be sensitized to the pathogen-related peptides by exposing the cells to the peptides and the β2-microglobulin ex vivo, for example by isolating a population of cells comprising antigen presenting cells from blood or from lymphoid organs from the mammalian host and pulsing the isolated antigen presenting cells with the pathogen-related peptides in the presence of β2-microglobulin ex vivo. The sensitized cells are then returned to the host, where they are exposed to a population of T lymphocytes. Alternatively, the T lymphocytes of the mammalian host can be exposed to the pathogen-related peptides and the β2-microglobulin by administering the pathogen related peptides and the β2-microglobulin in vivo, for example by subcutaneous injection.

In accordance with the present invention, a new use for purified $\beta_2$-microglobulin as an adjuvant for synthetic polypeptide vaccines is also provided.

BRIEF DESCRIPTION OF THE DRAWINGS

In FIG. 1A, LB27.4 APC's were pulsed with tOVA for 3 hours with or without human $\beta_2$-microglobulin; in FIG. 1B, EL4 APC's were pulsed for 2 hours With tOVA and human $\beta_2$-microglobulin and in FIG. 1C, EL4 APC's were pulsed for 0.5–2 hours with tOVA and human $\beta_2$-microglobulin.

For FIG. 2A and 2B, peptides with or without $\beta_2$-microglobulin were injected into the mammalian host as follows. Individual age and sex matched mice, one mouse per group, were injected subcutaneously in each flank (two sites per animal) with 94 µg of tOVA with or without 47 µg of purified $\beta_2$-microglobulin (Sigma Chemical Co., St. Louis, Mo.) in phosphate buffered saline (47 µl per injection site). After 7 days, the mice were sacrificed and the spleens harvested. Splenocytes ($30\times10^6$) were then stimulated with $15\times10^6$ 20,000 gamma irradiated EG7 cells (a transfected EL4 cell synthesizing OVA) in 10 mls of 10% FCS-containing RPMI 1640 at 37° C. After five days of incubation, the restimulated cells were tested as effectors in a standard $^{51}$Cr release assay. Targets were, in FIG. 2A, EL4 cells (no antigen), or EL4 cells precultured in 300 µg/ml tOVA for 18 hours at 37° C. in media with 10% FCS, and in FIG. 2B, EG7 cells (a transfected EL4 cell synthesizing OVA). Effector to target ratios were 11, 33 and 100. Data are expressed as % specific release versus effector to target (E:T) ratio.

Figure 2A:
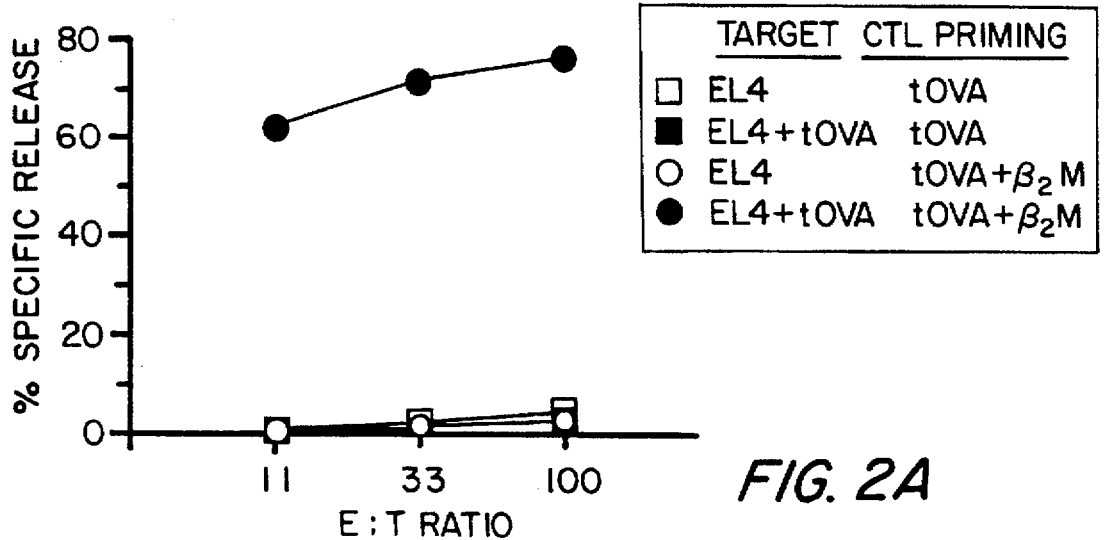
FIGS. 2A through 2E are graphical illustrations demonstrating that effective priming of cytotoxic T lymphocytes in vivo can be effected by presenting APC's with peptides and $\beta_2$-microglobulin.
Figure 2B:
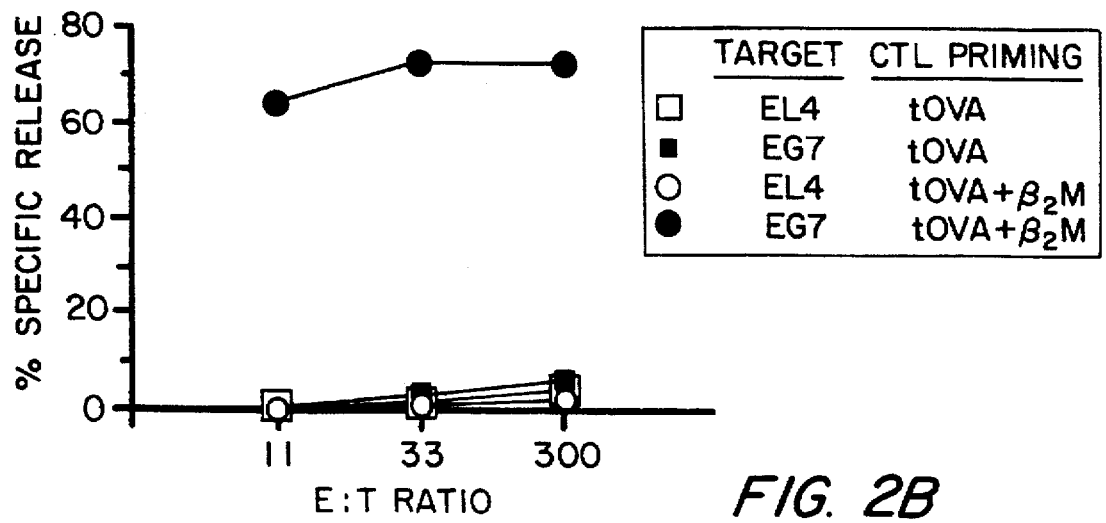
Figure 2C:
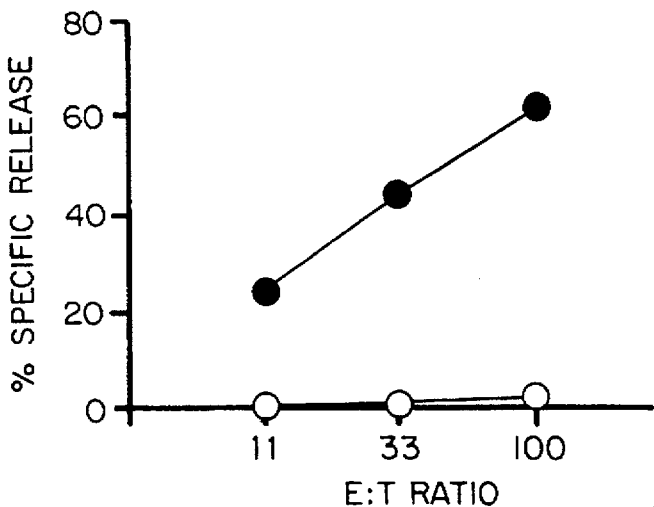

In FIG. 2C, splenocytes were incubated first with tOVA (800 µg/ml) and $\beta_2$-microglobulin (10 µg/ml) for 2 hours, washed and then incubated again without antigen or $\beta_2$-microglobulin. The cells were then irradiated and injected into the mice. Splenocytes from immunized mammals were cocultured and irradiated with EG7 cells and the presence of CTL's determined in a standard chromium release assay using EL4 (open circles) or EG7 (closed circles) as target cells. Data points are expressed as the mean % of specific release of chromium from labeled target cells.

Figure 2D:
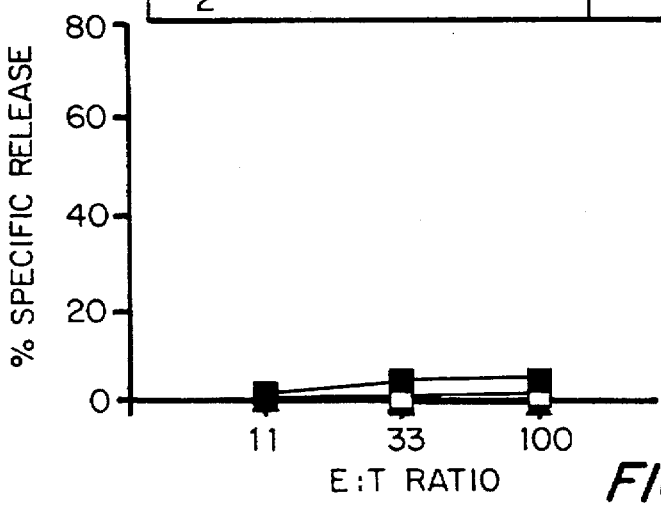

FIG. 2D is similar to FIG. 2C, except mice were unimmunized (squares) or immunized with splenocytes that were exposed to tOVA in the first incubation and $\beta_2$-microglobulin in the second incubation (triangles). All symbols are displayed, however several data points are overlapping.

Figure 2E:
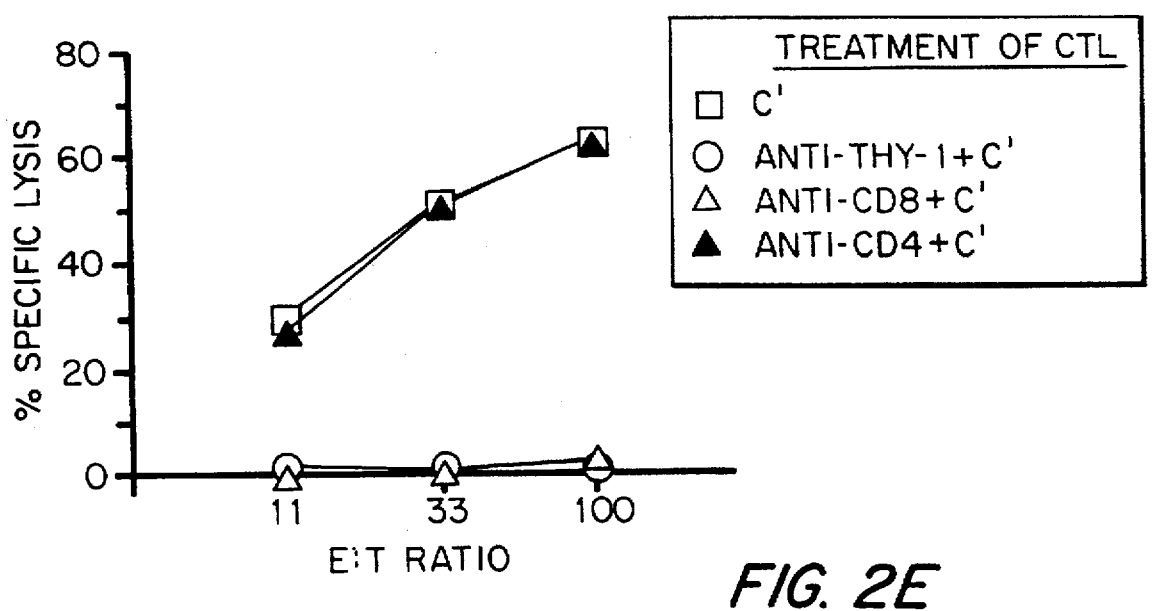

FIG. 2E illustrates that the effector cells that are primed with the OVA peptides and $\beta_2$-microglobulin are CD4-, CD8+ T cells. Cells that had been treated with anti-CD8 monoclonal antibody plus complement (open triangle) and anti-Thy-1 monoclonal antibody exhibited a total loss of cytolytic function against EG7 cells.

Figure 3:
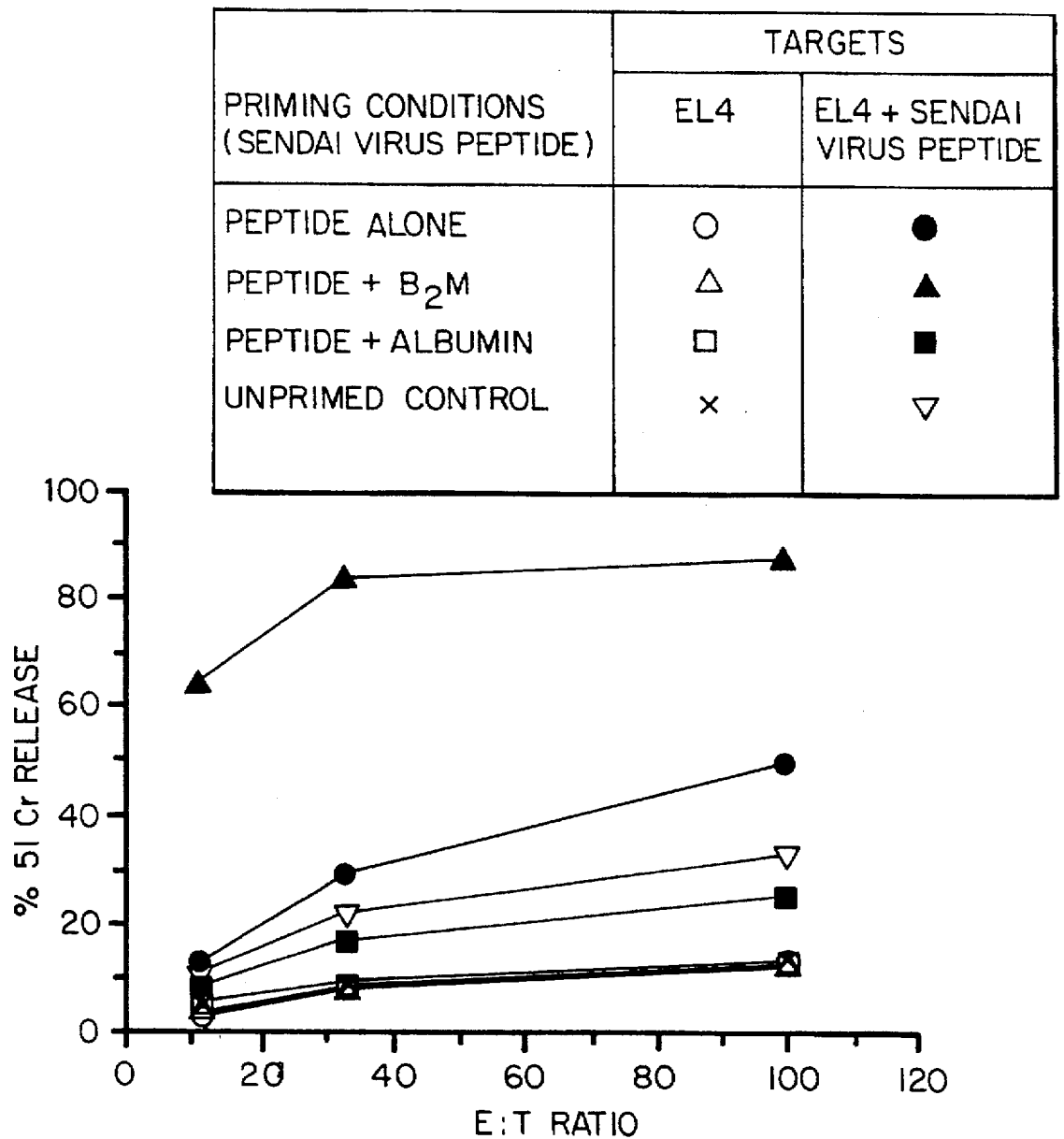

FIG. 3 is a graphical illustration demonstrating that CTLs are primed in animals that have been injected with Sendai virus peptides together with $\beta_2$-microglobulin, but not with peptides alone or peptides with another protein, human serum albumin. The open symbols represent chromium-labeled EL4 target cells, while the closed symbols represent chromium-labeled EL4 target cells primed with Sendai virus peptide. The data were obtained as described in Example 3A.

Figure 4:
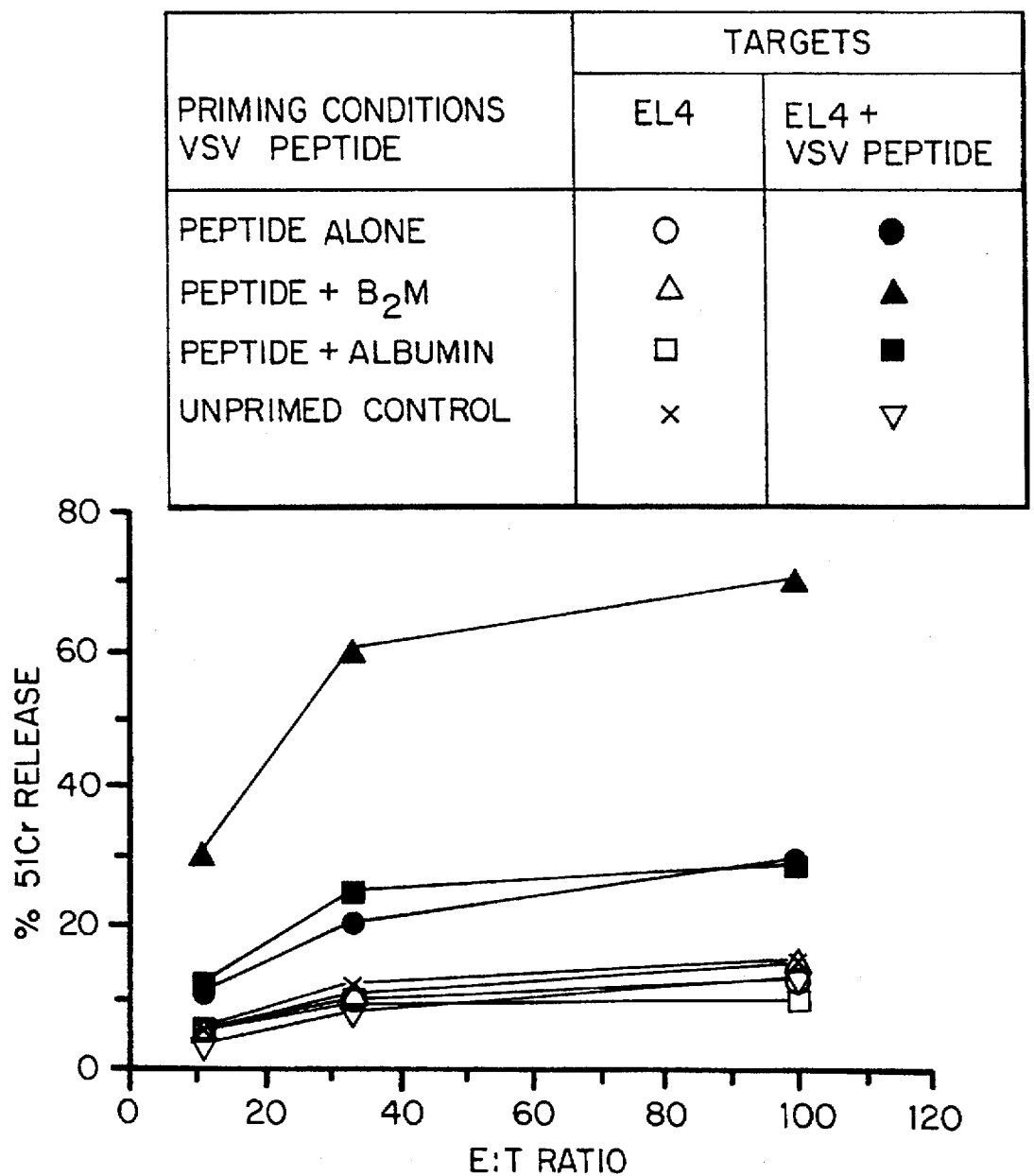

FIG. 4 is a graphical illustration demonstrating that CTLs are primed in animals that have been injected with vesicular stomatitis virus peptides together with $\beta_2$-microglobulin, but not with peptides alone or peptides with another protein, human serum albumin. The open symbols represent chromium-labeled EL4 target cells, while the closed symbols represent chromium-labeled EL4 target cells pulsed with vesicular stomatitis peptide. The data were obtained as described in Example 3B.

Figure 5A:
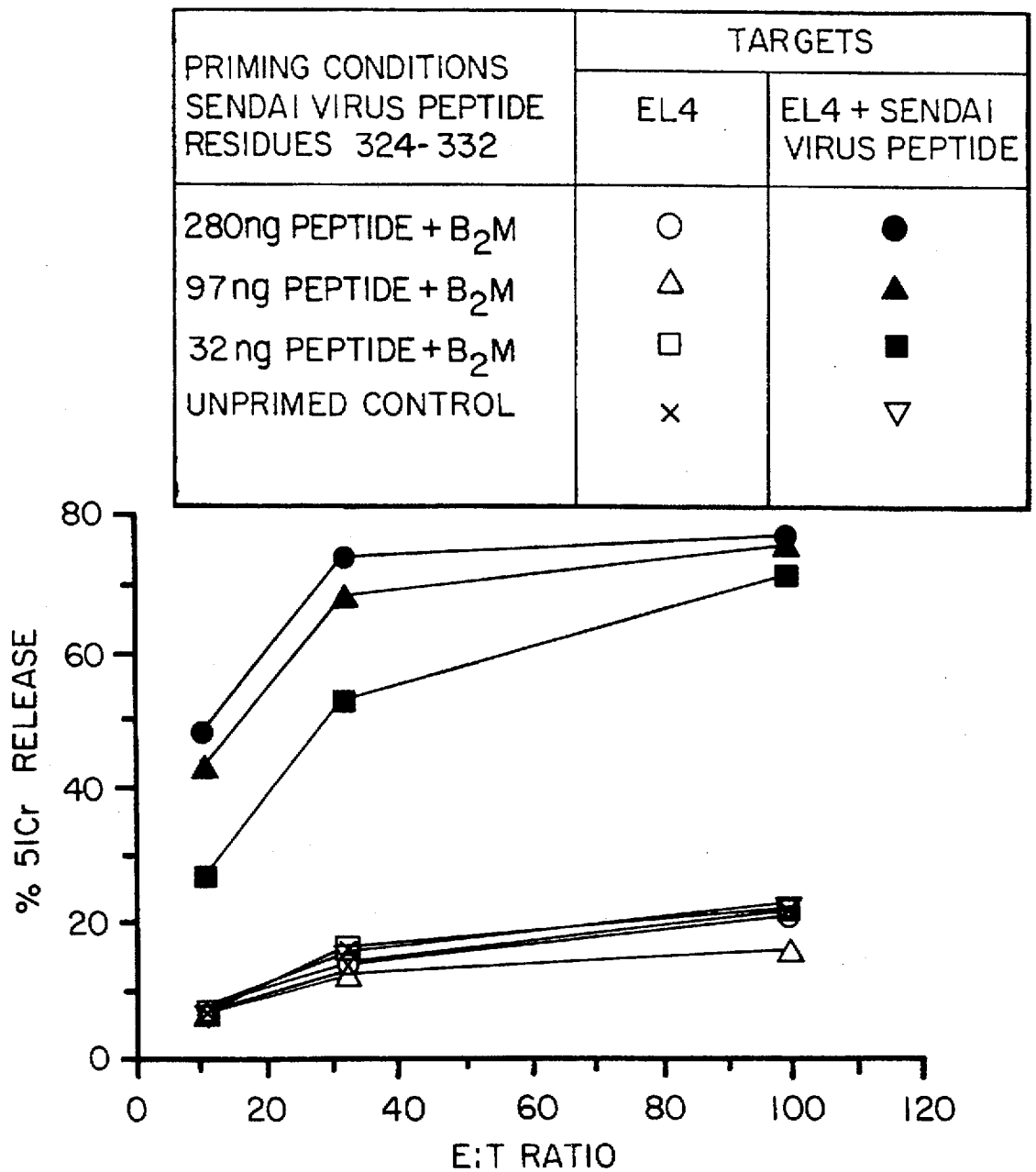
Figure 5B:
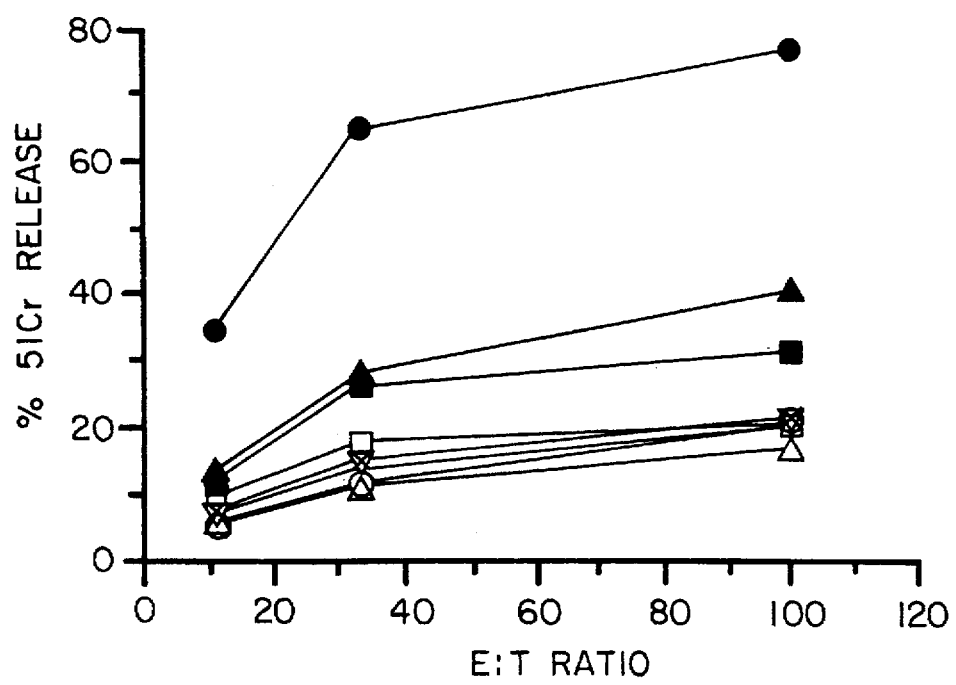

FIGS. 5A and 5B are graphical illustrations demonstrating that both a short form (FIG. 5A) and a long form (FIG. 5B) of the Sendai class I virus peptide prime CTL responses in vivo. The open symbols represent chromium-labeled EL4 target cells, while the closed symbols represent chromium-labeled EL4 target cells pulsed with Sendai virus peptide. In all cases, priming of CTL responses was highly dependent on the coinjection of $\beta_2$-microglobulin.

Figure 6:
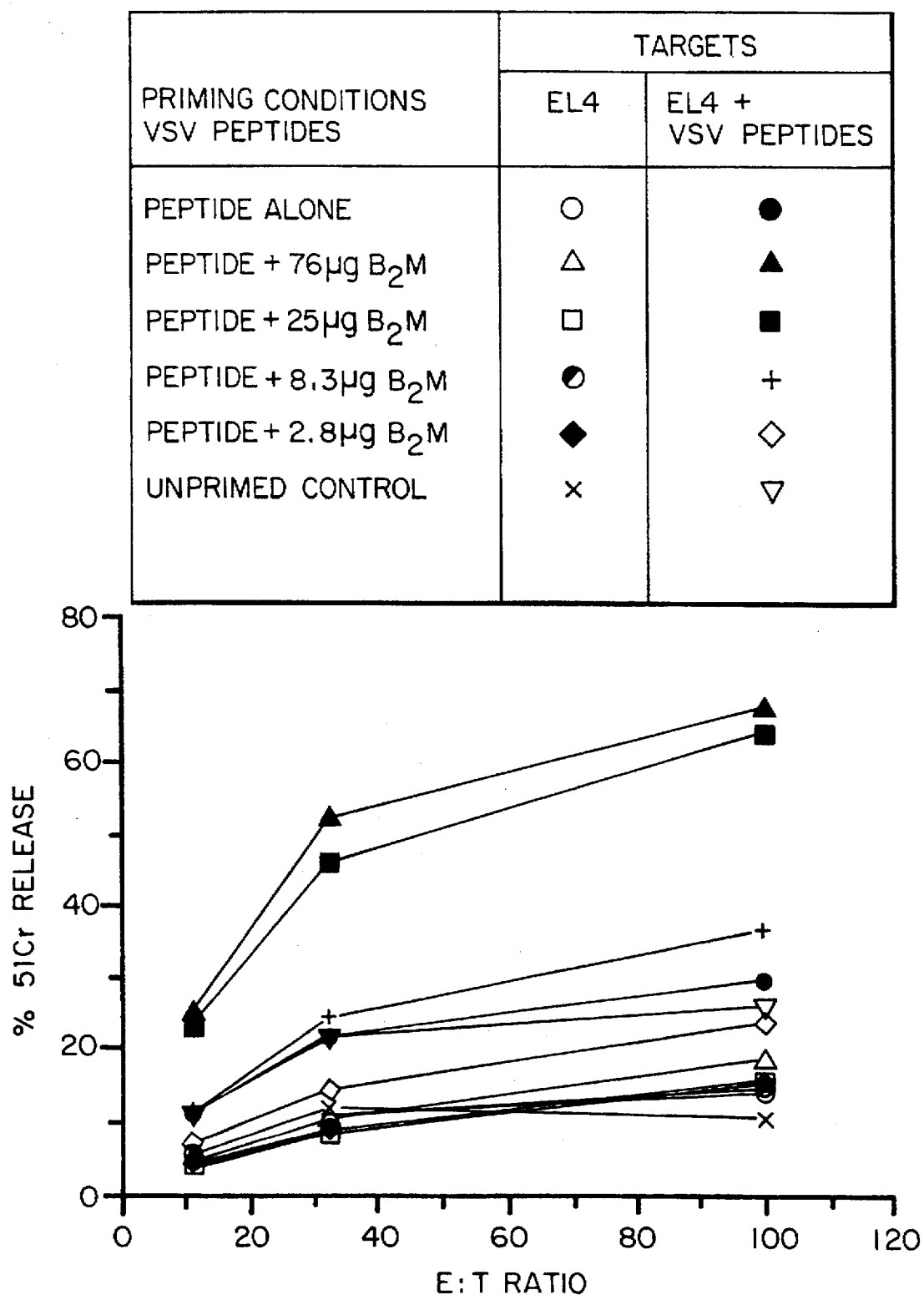

FIG. 6 is a graphical illustration demonstrating that CTLs were primed in animals that had been injected with 10 µg vesicular stomatitis virus peptides together with 76 or 25 µg $\beta_2$-microglobulin, with almost equal efficiency. Priming efficiency in the mice dropped off significantly between 25 and 8.3 µg of $\beta_2$-microglobulin.

DETAILED DESCRIPTION OF THE INVENTION

The major histocompatibility complex (MHC) is a chromosomal region consisting of a series of genes that code for the cell surface expression of strong transplantation antigens. These transplantation antigens are, in general, glycoproteins that are present on the surface of most nucleated cells. The MHC in mammals is also in the region where the histocompatibility-linked immune response genes are located; hence the chromosomal segment not only controls the synthesis of transplantation antigens and graft rejection, but also influences immune responses to infectious challenge and susceptibility to the development of immunologically mediated diseases. The two MHC systems that have been most extensively characterized are the H-2 system in the mouse and the HLA system in humans.

The MHC's of the mammals studied to date are remarkably similar, suggesting an evolutionary pressure for conservation of these genetic regions. In each instance, the genes code for two general types of antigen; class I and class II. The present invention relates to the association of peptide antigens with class I molecules.

The class I genes (HLA-A, B and C in humans, H-2K, D, L in mice) code for multi-determinant antigens which appear on the surface of cells as two peptide chains. Only the heavy chain is encoded by the MHC and contains hypervariable regions analogous to the immunoglobulins. The heavy chain peptide consists of a large transmembrane glycoprotein of about 44K molecular weight (350 amino acids). This heavy chain is usually non-covalently associated with the light chain, $\beta_2$-microglobulin, a 100 amino acid, 12K molecular weight protein. $\beta_2$-microglobulin is encoded by genes on a separate chromosome than those coding for the class I heavy chains. The present invention is based upon the discovery that the binding of exogenous peptides to class I MHC molecules on the surface of antigen presenting cells is facilitated in the presence of free $\beta_2$-microglobulin.

Although a small amount of free $\beta_2$-microglobulin is inherently present in mammalian serum, and hence in some serum-containing culture media used in in vitro sensitization and priming experiments, it has never been recognized or suggested that a component in serum might facilitate the association of peptides with class I molecules. A role for free $\beta_2$-microglobulin was previously unknown.

The present invention provides a method for markedly enhancing the association of exogenous peptides to class I MHC molecules on the surface of antigen presenting cells. The method comprises the steps of obtaining the exogenous peptides of interest and presenting the peptides extracellularly to antigen presenting cells bearing class I molecules in the presence of elevated levels of exogenous free $\beta_2$-microglobulin. This method can be utilized to enhance the efficiency of the sensitization of target cells with antigen in vitro, and to prime naive populations of T lymphocytes for antigen-specific cytotoxic T cell responses, both in vitro and in vivo. The invention is thus useful in the study of class I MHC antigen presentation and cell-cell interaction and is also useful for enhancing the immunogenicity of synthetic peptides in vaccines.

In a preferred embodiment, $\beta_2$-microglobulin is used as an adjuvant in vaccination of a host organism with exogenous peptides which mimic epitopes of a pathogenic organism or malignant disorder against which protection is sought. In accordance with this embodiment, the mammalian host is immunized with the exogenous class I peptides and free $\beta_2$-microglobulin such the $\beta_2$-microglobulin is present at the time of pulsing the antigen presenting cells of the host mammal with the peptides. When administered in effective amounts in the presence of an elevated level of free $\beta_2$-microglobulin, the peptides are capable of priming effector and memory class-I restricted cytotoxic T lymphocytes which immunoreact with the exogenous peptides.

As used herein, the phrase "free $\beta_2$-microglobulin" has its conventional meaning in the published literature and refers to $\beta_2$-microglobulin peptides that are unbound to the heavy chain of class I MHC. The term "sensitize" refers to the association of peptides with MHC molecules on antigen presenting cells. The sensitization of class I MHC antigen presenting cells can be determined by assaying for antigen/ class I-specific response with CTL's or T-T hybridomas that recognize antigen in association with the class I restriction pattern. "Priming" refers to the initiation or activation of cytotoxic T lymphocyte response from a population of cells comprising a naive population of lymphocytes, i.e. a population of T lymphocytes that has not previously been exposed to the antigen.

The words "polypeptide" and "peptide" are used interchangeably and designate a linear sequence of amino acids connected one to the other by peptide bonds between the alpha amino and carboxyl groups of adjacent amino acids. The peptides can be of a variety of lengths, either in their neutral (uncharged) form or in forms such as their salts and either free of modifications such as glycosylations, side chain oxidation or phosphorylation or containing such modifications. Also included in the definition are peptides modified by additional substituents attached to the amino side chains, such as glycosyl units, lipids or inorganic ions such as phosphates as well as chemical modifications of the chains. Thus, the term "peptide" or its equivalent is intended to include the appropriate amino acid sequence referenced, subject to the foregoing modifications, which do not destroy its functionality.

The term "epitope" herein refers to that portion of a molecule, usually a protein, that is specifically bound by a T cell receptor or an antibody combining site. The term is also used interchangeably with "antigenic determinant".

The exogenous peptides that can be used in accordance with the method of the present invention are not particularly limited, as long as at least some of the peptides administered can bind to the specific class I MHC molecules of the mammalian host to be immunized. In view of the polymorphism of class I MHC molecules in the population, the class I peptides preferably will comprise a mixture or "cocktail" of peptide epitopes from antigenic proteins of pathogenic organisms or malignant tissue that can be recognized by a variety of different HLA-types. Alternatively, the class I peptides can be precisely tailored to the MHC alleles of the host to be immunized.

The protein antigens of a number of pathogens and malignant tissues are known from the scientific literature, as are peptides from such antigens that bind to a particular HLA-type. These peptides range in length from about eight to twenty, and usually from about eight to ten, amino acid residues. Such peptides are sometimes referred to as class I peptides. Thus, in many instances, the peptides used in accordance with the present invention will be antigenic determinants that have previously been shown to be recognized in connection with a particular MHC molecule by cytotoxic T lymphocytes in vitro.

For example, various synthetic peptides derived from the influenza virus have been shown to induce cytolytic T cell activity in vitro, but not in vivo. These include peptides from the influenza nucleoprotein composed of residues 365-80 (NP365-80), NP50-63, and NP147-58 and peptides from influenza hemagglutinin HA202-21 and HA523-45, defined previously in class I restricted cytotoxicity assays. See, Perkins et al, *J. Exp. Med.*, Vol. 170, 279–289 (July 1989). Enhanced efficiency of association of such polypeptides to specific class I molecules on antigen presenting cells in vivo has major implications for the use of these synthetic peptides as influenza vaccines. Other examples of synthetic peptides containing known epitopes that can be recognized by MHC-restricted CTLs include influenza strain A/Jap/57 hemagglutinin protein, residues 508–530; influenza strain A/PR8/34 nucleoprotein residues 360–385; HIV Pol (reverse transcriptase) residues 203–219; Sendai virus nucleoprotein peptide, residues 324–332; and the vesicular stomatitis nucleotide protein, amino acid residues 52–59. In addition, antigenic determinants of proteins involved in malignant disorders can also be used to protect against malignant disease.

This list of peptides is exemplary only and is not intended to limit the class I peptides with which the method of the present invention can be employed. The class I peptides that can be used with the present invention can also be determined empirically in accordance with techniques known in the art. For example, the peptides that are displayed by a variety of different class I molecules can be defined for a given pathogen-related antigen by infecting somatic cells of given class I HLA types with the pathogen of interest. The peptides that bind to the class I molecules after normal intracellular processing are then eluted from the target cell surface and subjected to sequence analysis in accordance with known techniques. Alternatively, overlapping peptides from a given pathogen-related protein can be synthesized and analyzed for their ability to bind to the various class I HLA types.

In accordance with the present invention, the association of the class I peptides to class I molecules on the surface of antigen presenting cells can be enhanced, to thereby enhance the immunogenicity of any class I peptide.

The peptides used in accordance with the method of the present invention can be obtained in any one of a number of conventional ways. Because they will generally be short sequences, they can be prepared by chemical synthesis using standard techniques. Particularly convenient are the solid phase peptide synthesis techniques. Automated peptide synthesizers are commercially available, as are the reagents required for their use. Alternatively, the peptides can be prepared by enzymatic digestion or cleavage of naturally occurring proteins. The peptides can also be prepared using recombinant techniques known to those of skill in the art, although this is not the most efficient approach for making peptides of shorter length.

The $\beta_2$-microglobulin used in the invention can be obtained from a variety of sources, including, for example, human, murine, bovine, equine or other mammalian serum or body fluids normally containing a small amount of free $\beta_2$-microglobulin. Mixtures of β2-microglobulin from these sources can also be used. Purified human $\beta_2$-microglobulin is available commercially, for example from Sigma Chemical Co., St. Louis, Mo. Alternatively, $\beta_2$-microglobulin can be isolated and purified from serum or other body fluids using conventional techniques or can be produced by recombinant techniques based upon the introduction of $\beta_2$-microglobulin genes into appropriate expression systems. The human and murine genes encoding $\beta_2$-microglobulin have previously been cloned. In addition, their sequences are known, thus allowing for the isolation of a DNA clone from these or other species.

When used as an adjuvant for vaccination with peptides, it may be preferable to use $\beta_2$-microglobulin originating from the same species as the vaccine recipient in order to reduce the possibility of an immune response to the exogenous free $\beta_2$-microglobulin. Our research has shown, however, that $\beta_2$-microglobulin is not intrinsically inflammatory in vivo and hence xenogeneic $\beta_2$-microglobulin can also be used as the adjuvant. In some instances, xenogeneic $\beta_2$-microglobulin may actually have a greater affinity for class I molecules, and hence comprise a preferred adjuvant for enhancing immunogenicity of the peptides in vivo.

In accordance with the present invention, an increased number of antigen-class I complexes will occur in the presence of $\beta_2$-microglobulin at any point in time. It is expected that more complexes will form at higher concentrations of $\beta_2$-microglobulin. More antigen-MHC-class I complexes will result in a stronger and more persistent stimulation, and hence, higher concentrations of $\beta_2$-microglobulin are most desirable.

The concentration of free $\beta_2$-microglobulin in extracellular mammalian body fluids, such as adult mammalian serum, is very low and hence its ability to facilitate the association of extracellular peptides with class I MHC molecules is limited. For in vivo applications, the amount of free $\beta_2$-microglobulin administered to the host must be sufficient to increase the concentration of free $\beta_2$-microglobulin in the extracellular body fluids above the level normally present, for example, in mammalian serum, in order to favor the binding of $\beta_2$-microglobulin and peptides to class I MHC heavy chains and stimulate an immune response. The concentration of $\beta_2$-microglobulin can be elevated systemically, i.e. throughout the body by increased levels in the blood, or locally at the site of injection. The latter is more attractive clinically and economically, and hence is preferred. While the amount of $\beta_2$-microglobulin required to stimulate a peptide-specific immune response may vary to some degree depending upon the exogenous peptide for which the immune response is desired and the mammal to be immunized, the determination of the optimal amount of $\beta_2$-microglobulin for a given vaccination protocol is within the skill of the art.

Normal ranges of $\beta_2$-microglobulin concentration in mammalian serum and other extracellular fluids are readily ascertainable and in many instances are available in the published literature. Adult human $\beta_2$-microglobulin, for example, is normally present in serum in an amount of about 1.5–2 µg/ml. See, "Trace Components of Plasma: Isolation and Clinical Significance," Jamieson, G. A. Ed., Alan R. Liss, Inc. Publisher, New York, N.Y. (1976). The concentration of free $\beta_2$-microglobulin in normal adult mouse serum is also about 1–2 µg/ml. Natori et al., *J. Immunogenet*, 3, 123–134 (1976). The phrase "elevated $\beta_2$-microglobulin concentration" thus refers to a concentration that is greater than that normally present in the extracellular fluids, preferably serum, of a mammal of the same species as the host and which is sufficient to stimulate a peptide-specific immune response. Precise amounts of $\beta_2$-microglobulin can be tailored to the particular application and peptides used in the immunization.

To determine the optimal dosages of free $\beta_2$-microglobulin for stimulating a cytotoxic T lymphocyte response to a peptide(s) in a human being, human patients are immunized with differing dosages of peptides that are known to be presented with the individuals' HLA molecules and $\beta_2$-microglobulin. The peptides are titrated over several logs range of concentration (1 ng to mgs.) and the $\beta_2$-microglobulin titrated over several logs (e.g. 0.015 to 150 mg). After one to several weeks, peripheral blood mononuclear cells are isolated from the patients and prepared using conventional techniques, restimulated with the appropriate antigen in vitro under standard conditions, and the development of specific cytotoxic T lymphocytes assayed in standard CTL assays. Populations at risk are immunized with the predetermined effective doses and analyzed prospectively versus controls for the incidence of disease to determine the degree of protection conferred. The amount of $\beta_2$-microglobulin administered by local inoculation will typically range from about 0.025 mg to about 50 mg per site, preferably about 0.050 mg to 25 mg per site. For systemic administration, inoculations of $\beta_2$-microglobulin may contain about 0.5 to about 250 mg/kg of body weight.

With respect to potential toxicity of the adjuvant, local reaction to injections or other morbidity of animals immunized with $\beta_2$-microglobulin has not been observed. Elevated levels of $\beta_2$-microglobulin are unlikely to be toxic in vivo since high levels are normally present during mammalian fetal development. Further, $\beta_2$-microglobulin is effective when injected subcutaneously in aqueous solution which is an effective and well tolerated immunization protocol. $\beta_2$-microglobulin thus has favorable characteristics for an adjuvant.

The effective amount of exogenous polypeptide in a unit dose depends upon a number of factors. Included among these factors are the nature of the carrier, if one is used, the amount of $\beta_2$-microglobulin, the number of inoculations to be used and, to some extent, the body weight of the mammal to be immunized. Individual local inoculations will typically contain about one micrograms to about five milligrams of polypeptide. For systemic administration, inoculations may typically contain about 0.5 to 3 mg/kg of body weight. To achieve a useful level of protection in a population with synthetic peptides, a variety of peptide epitopes, derived from various subunits of the pathogen will preferably be employed, since MHC molecules are known to be polymorphic. Alternatively, where a specific peptide is known to be reactive with a particular MHC class I molecule, individuals with that MHC-specificity can be specifically immunized with the peptide. In addition to the class I restricted peptides, the vaccine can additionally include class II MHC-restricted peptides.

The preparation of vaccines which contain peptide sequences as active ingredients is well understood in the art. Typically, such vaccines are prepared as injectables, either as liquid solutions or suspensions. The active ingredients are often mixed with excipients which are pharmacologically acceptable and compatible with the active ingredient. Suitable excipients are, for example, water, saline, dextrose, glycerol, ethanol, or the like and combinations thereof, with saline being particularly preferred. In addition, and in accordance with the present invention, the vaccine contains free $\beta_2$-microglobulin as an adjuvant which enhances the effectiveness of the vaccine.

The vaccines are conventionally administered by injection, for example either subcutaneously or intramuscularly. In accordance with the present invention, the exogenous peptides which are the active ingredients of the vaccine are presented to antigen presenting cells of the immune system in the presence of elevated levels of free $\beta_2$-microglobulin. Thus, in one embodiment, the exogenous peptides and free $\beta_2$ can be prepared as an injectable and simultaneously injected into the mammal to be immunized. The peptides and $\beta_2$-microglobulin can either be free in the liquid solutions or suspensions or can be encapsulated in a depot or other controlled release vehicle. Booster injections can be given, if needed.

In an alternative embodiment, the host cells can be sensitized to the peptides by isolating a population of cells comprising antigen presenting cells from the blood or lymphoid organs from the mammalian host in accordance with established techniques and pulsing the isolated antigen presenting cells with the peptides comprising at least one pathogen-related peptide in the presence of $\beta_2$-microglobulin ex vivo. The cells comprising antigen-presenting cells can be isolated, for example, from peripheral blood by drawing a sample of blood from the patient and isolating the mononuclear lymphoid elements in accordance with established protocols. The mononuclear cells are then sensitized with about 10–100 µg/ml $\beta_2$-microglobulin and 0.01 to 800 µg/ml of the exogenous peptides. Sensitization can be effected by incubating about $1-10\times10^7$ of the mononuclear lymphoid cells in appropriate media in the presence of the peptides and $\beta_2$-microglobulin. After about 1 to 4, and preferably about 2 hours, the cells are washed, irradiated and then returned to the patient, preferably by intravenous inoculation, although other clinically acceptable inoculations can alternatively be employed. The critical feature is that the peptides are presented to the antigen presenting cells in the presence of free $\beta_2$-microglobulin and any method utilized to accomplish such result is considered to be within the spirit and scope of this invention.

The present invention will be more clearly understood from the following specific examples.

EXAMPLE 1

In Vitro Target Cell Sensitization With $\beta_2$ Microglobulin

This example demonstrates that the efficiency of association of exogenous peptides with $K^b$ class I MHC can be significantly enhanced by increasing the amount of free $\beta_2$-microglobulin present in the incubation media.

In the experiment, antigen presenting cells ("APC's") were pulsed with peptides obtained from a tryptic digest of ovalbumin ("tOVA") prepared as described in Shimonkevitz et al., *J. Exp. Med.*, 158:303–316 (1983), in media containing low amounts of serum and in the presence or absence of purified human $\beta_2$-microglobulin as follows.

Antigen presenting cells were EL4 cells, (an H-2$^b$, Class I+, Class II−, T lymphoblastoid cell line) or LB27.4 cells, an H-2$^{bxd}$, Class I$^+$, Class II+, lymphoblastoid cell line. The APC's, which had been adapted to grow in serum-free media (SFM)(OPTIMEM media, Gibco, Grand Island, N.Y.) supplemented with 1% SP-NUTRIDOMA media (Boehringer Mannheim, Indianapolis, Ind.) supplemented with 1% normal mouse serum, were incubated with or without 100 or 300 µg/ml tOVA in complete SFM, 1% NMS and with the addition of purified $\beta_2$-microglobulin (Sigma Chemical CO., St. Louis, Mo.) at (a) 2.5 µg/ml. (b) 0.1 µg/ml and (c) 0.1–9 µg/ml. After 2–3 hours of incubation at 37° C., the APC's were fixed with paraformaldehyde and added to cultures with RF33.70. OVA-K$^b$-specific T-T hybridomas which secretes interleukin-2 upon appropriate antigenic stimulation. Rock et al., *J. Immunol.*, 145:804–811 (Aug. 1, 1990). Microcultures were prepared with 5–10×10$^4$ T-T hybridomas with a titration of tOVA and with or without 5×10$^4$ fixed antigen presenting cells in RPMI 1640-10% fetal calf serum (FCS) media.

Figure 1A:
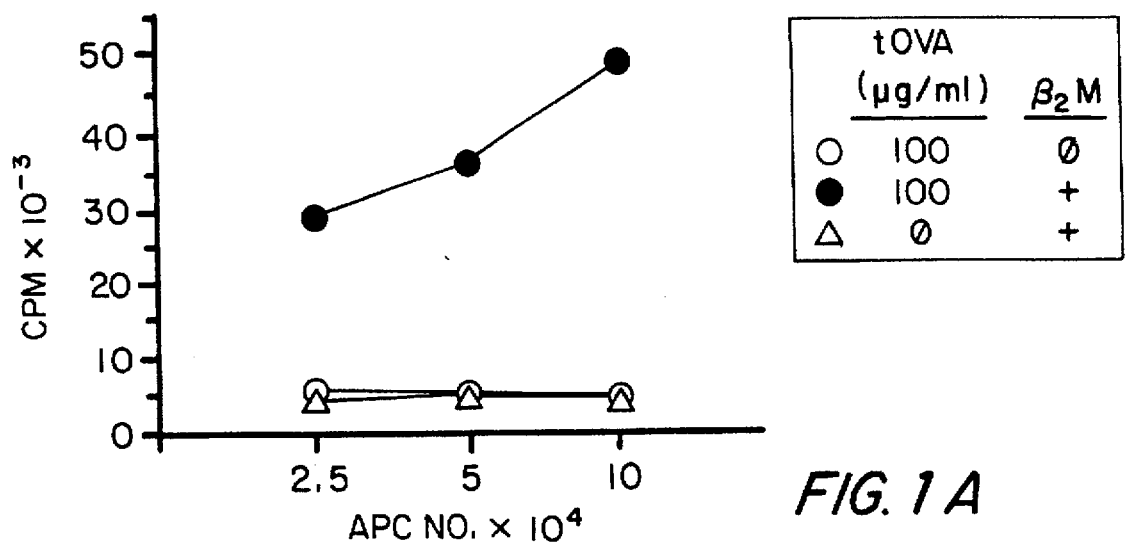
FIGS. 1A and 1B are graphical illustrations which show that exogenous tOVA peptides rapidly associate with class I MHC molecules on the surface of antigen presenting cells in vitro in the presence of exogenous, purified $\beta_2$-microglobulin. Antigen presenting cells (APCs) were incubated in the presence or absence of the indicated concentrations of human $\beta_2$-microglobulin. After 2–3 hours incubation at 37° C. the APC's were fixed and added to cultures with the RF33.70 hybrids (anti-Ova+$K^b$ specific T-T hybrid). Antigen presenting cells were EL4 APC's (an H-$2^b$, Class I$^+$, Class II$^-$ lymphoblastoid cell line) or LB27.4 APC's (an H-$2^{bxd}$, Class I$^+$, Class II$^+$, B lymphoblastoid cell line).
Figure 1B:
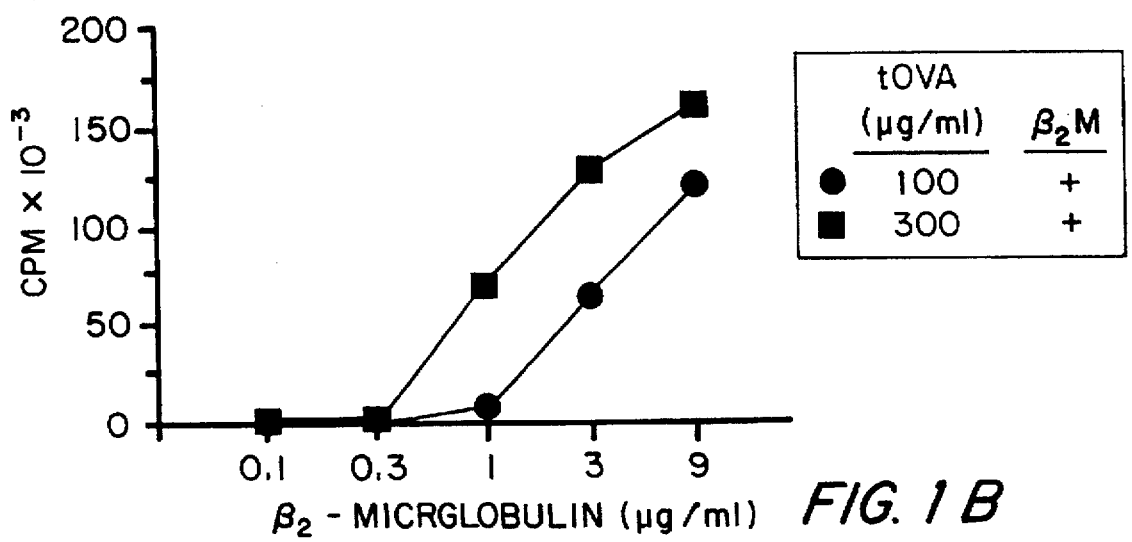
Figure 1C:
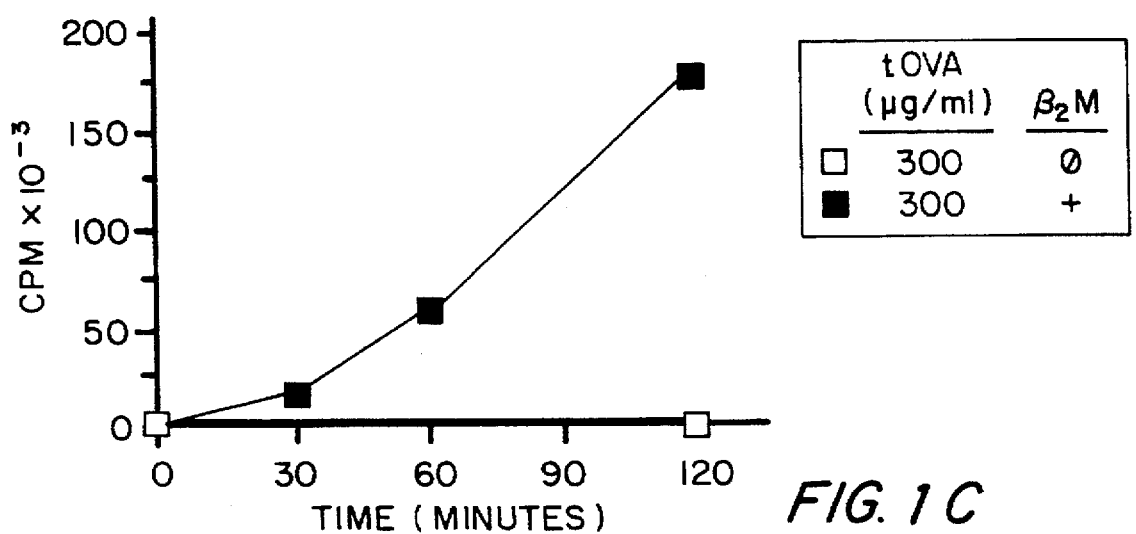

The results of this study demonstrate that peptide rapidly associates with class I MHC molecules in the presence of exogenous, purified $\beta_2$-microglobulin. In the presence of exogenous $\beta_2$-microglobulin, there is extremely effective pulsing of class I MHC molecules on both APC's (FIG. 1). Under these conditions, the association of peptide is rapid and can be detected after 30–60 minutes (FIG. 1A). The optimal concentration of $\beta_2$-microglobulin under these conditions is greater than 9 µg/ml. At low concentrations, such as are present in typical culture media containing 10% serum, the formation of OVA-class I molecules is not detectable in this time period (FIG. 1B). Thus, in accordance with the present invention, the association of peptide with class I MHC molecules on the surface of antigen presenting cells can be enhanced by increasing the amount of free $\beta_2$-microglobulin to a concentration greater than that normally found serum.

EXAMPLE 2

In Vivo Immunization

This experiment establishes that the method of the present invention can be utilized to induce cytotoxic T lymphocyte response in vivo.

In vivo sensitization and priming

Individual age and sex matched C57BL6 mice, one per group, were injected subcutaneously in each flank (two sites per animal) with 94 µg of tOVA with or without 47 µg of purified $\beta_2$-microglobulin (Sigma Chemical Co., St. Louis, Mo.) in phosphate buffered saline (47 µl per injection site). The total amount of tOVA injected into each animal was thus 188 µg; total $\beta_2$-microglobulin was 94 µg. After 7 days, the mice were sacrificed and the spleens harvested. Splenocytes (30×10$^6$) were then stimulated with 15×10$^6$ 20,000 gamma irradiated EG7 cells (a transfected EL4 cell synthesizing OVA) in 10 mls of 10% FCS-containing RPMI 1640 at 37° C.

After five days of incubation, the restimulated cells were tested as effectors in a standard $^{51}$Cr release assay. Targets were EL4 cells (no antigen), EL4 cells precultured in 300 µg/ml tOVA for 18 hours at 37° C. in media with 10% FCS, or EG7 cells (a transfected EL4 cell synthesizing OVA).

As illustrated in FIGS. 2A and 2B, injection of tOVA and $\beta_2$-microglobulin into unprimed mice induced a significant cytotoxic T lymphocyte response; restimulated spleen cells lysed EL4 APC's in the presence of tOVA, but not in the presence of APC's alone. Consistent with previous reports in the literature (See, Carbone and Bevan, *J. Exp. Med.*, Vol. 169, pp. 603–11 (March 1989)), no priming was obtained with tOVA in the absence of $\beta_2$-microglobulin. This control establishes the criticality of an elevated level of $\beta_2$-microglobulin for in vivo priming with peptides. FIG. 2B illustrates that priming with peptides and $\beta_2$-microglobulin stimulated CTL that can recognize the naturally produced/processed form of OVA (EG7 cells), which is important for vaccine applications.

The results of this study demonstrate that normal APC's exposed in vivo to exogenous peptide in the presence of an elevated level of $\beta_2$-microglobulin will acquire the peptides in a manner which allows for the priming of antigen specific cytotoxic T lymphocytes.

Ex vivo sensitization of antigen presenting cells

To further examine whether peptide-MHC class I complexes formed on cells in the presence of exogenous $\beta_2$-microglobulin could prime CTL response in vivo, we injected naive animals with gamma-irradiated splenocytes that had been incubated ex vivo with tOVA in the presence or absence of human $\beta_2$-microglobulin as follows.

Cellular immunogens were prepared by incubating C57BL/6 splenocytes (4×10$^7$/ml) with t OVA (800 µg/ml) and $\beta_2$-microglobulin (10 µg/ml) for two hours at 37° C., washed and then incubated again for one hour without peptide or $\beta_2$-microglobulin. The cells were then irradiated in accordance with established techniques and injected intravenously into 57B1/6 mice.

After seven days, the animals were sacrificed and their spleens harvested. Spleen cells from these immunized animals were cocultured with irradiated EG7 cells in vitro for five days and assayed for the presence of CTLs using a chromium release assay using EL4 cells (open circles in FIG. 2C) or EG7 (closed circles). Data are expressed as the mean % specific release [$^{51}$Cr] from target cells.

In a similar experiment, mice were not immunized (square symbols in FIG. 2D) or were immunized with splenocytes that had been incubated with tOVA in the first incubation and $\beta_2$-microglobulin in the second incubation (triangle symbols in the drawing).

The results of these experiments, which are graphically illustrated in FIGS. 2C and 2D, revealed that anti-OVA CTL's were primed in animals injected with the lymphoid cells that had been incubated with both tOVA and $\beta_2$-microglobulin but not with cells that had only been exposed to tOVA in the first incubation. Similar results were obtained with a synthetic peptide (OVA$_{257-264}$).

Phenotype of cells mediating the antigen-specific killing

We next examined the phenotype of cells that mediated antigen-specific killing. Splenocytes from mice that had been injected simultaneously with tOVA and β2-microglobulin were restimulated with EG7 cells, as described above. The cells from these cultures were then treated with media, anti-Thy-1 mAb (M5/49), anti-CD8 mAb (ADH4) or anti-CD4 mAb (GK1.5) and complement, as previously described by Rock et al., *J. Immunol.*, 125:243 (1982), and were assayed for cytolytic activity against EG7 cells. The background specific release using EL4 cells as targets was 2.6, 7.9, and 18.6 at ratios of 11:1, 33:1, and 100:1, respectively. Animals were immunized with tOVA (100 µg) and human β2-microglobulin as described above. The restimulation of CTLs and Cr release assay were also performed as described.

As illustrated in FIG. 2E, the CTL effector cells were eliminated by treatment with anti-Thy-1 mAb plus complement. These cells were also removed by anti-CD8 mAb plus complement, but were insensitive to anti-CD4 mAb plus complement treatment. These data indicate that the killer cells generated in our system are CD8 positive, CD4 negative cells. This is the classical phenotype of CTLs.

MHC-specificity of the cytotoxic T lymphocytes

To determine the MHC-specificity of the cytotoxic T lymphocytes primed in vivo with the tOVA peptides, we tested the ability of various anti-MHC monoclonal antibodies to inhibit the killing of target cells. Splenocytes primed in vivo with tOVA and $\beta_2$-microglobulin were restimulated with irradiated EG7 cells and assayed for cytolytic activity against EL4 cells or EG7 cells. Animals were immunized with tOVA (100 μg) and human $\beta_2$-microglobulin as described herein. The restimulation of CTL's and $^{51}$Cr release assay were performed as described except that anti-K$^b$ mAb (BS-24-3)(Kohler et al., *Immune Syst.*, 2:202–208 (1981) or anti D$^b$ mAb (28.14.SS)(Ozato et al., *J. Immunol.*, 125:2473 (1980) (30 μg/ml) were added to the $^{51}$Cr release assay.

EG7 cells express class I but not class II molecules of the H-2b haplotype. Anti-Kb mAb markedly inhibited the killing of EG7 cells. In contrast, anti-Db mAb did not inhibit this response. These results argue that the CTLs are H2-kb restricted.

EXAMPLE 3
Priming Of CTLs Specific For Immunodominant Viral Epitopes

In light of the results of the in vitro and in vivo experiments, it was fully anticipated that $\beta_2$-microglobulin would promote the priming of CTL responses to other class I-restricted peptides. We therefore synthesized class I peptides corresponding to immunodominant epitopes from several pathogen-related viral proteins that have previously been defined and tested them as described below. This Example confirms that $\beta_2$-microglobulin promotes the priming of a CTL response to other immunodominant epitopes in vivo.

Experiment A—Sendai Virus Peptides

Individual age and sex matched C57BL/6 mice, once per group, were injected subcutaneously in each flank (two sites per animal) with 440 ng of Sendai virus nucleoprotein peptide comprising amino acid residues 324–332, with or without 76 μg of human $\beta_2$-microglobulin (Sigma Chemical Co.) of 76 μg of human albumin in PBS (Sigma). The Sendai virus nucleoprotein peptides, which were synthesized at the Dana-Farber Cancer Institute, in its Core Molecular Biology facility using conventional peptide synthesis techniques, correspond to the natural and optimal peptides sequences that bind to class I molecules (Schumacher et al., *Nature*, 350:703–706 (1991)). Total amount of Sendai virus peptides injected was 880 ng; total $_2$-M of albumin was 76 μg. After seven days the mice were sacrificed and their spleens removed.

Splenocytes were then stimulated with peptide pulsed irradiated spleen as a source of antigen-bearing antigen-presenting cells in media supplemented with fetal calf serum and rat con A supernatant for five days at 37° C. After the five days of incubation, the restimulated cells were tested as effectors in a standard $^{51}$Cr release assay. Targets were EL4 cells (no antigen), EL4 cells precultured with 10 μg/ml Sendai virus peptides for 18 hours at 37° C. in media with 10% FCS.

As shown in FIG. 3, CTLs were primed in animals that had been injected with the Sendai virus peptides together with $\beta_2$-microglobulin. Similar to the results obtained with the tOVA peptides, injection of peptide alone failed to elicit a CTL response; peptide with another human protein, human albumin, also failed to prime CTL responses. We have also failed to obtain priming when animals were injected with 10–1000 fold more peptide in the absence of $\beta_2$-microglobulin, indicating the high peptide concentration is not always sufficient to promote a CTL response in vivo.

Experiment B—Vesicular Stomatitis Virus Peptides

Individual age and sex matched C57BL/6 mice, once per group, were injected subcutaneously in each flank (two sites per animal) with 440 ng of vesicular stomatitis nucleoprotein virus peptide comprising amino acid residues 52–59, with or without 76 μg of human $\beta_2$-microglobulin (Sigma Chemical Co.) or 76 μg of human albumin in PBS (Sigma). The vesicular stomatitis nucleoprotein virus peptides correspond to the natural and optimal peptides sequences that bind to class I molecules (VanBleek and Nathenson, *Nature*, 348:213–216 (1990) and were prepared at the Dana-Farber Cancer Institute, Core Molecular Biology Facility. Total amount of vesicular stomatitis virus peptides injected was 880 ng; total β2-M of albumin was 76 μg. After seven days the mice were sacrificed and their spleens removed. Splenocytes were then stimulated with peptide pulsed irradiated spleen as a source of antigen-bearing antigen-presenting cells in media supplemented with fetal calf serum and rat con A supernatant for five days at 37° C.

After the five days of incubation, the restimulated cells were tested as effectors in a standard $^{51}$Cr release assay. Targets were EL4 cells (no antigen), EL4 cells precultured with 10 μg/ml vesicular virus peptides for 18 hours at 37° C. in media with 10% FCS.

As shown in FIG. 4, CTLs were primed in animals that had been injected with the vesicular stomatitis virus peptides together with $\beta_2$-microglobulin. Similar to the results obtained with the tOVA peptides and the Sendai virus peptides, injection of peptide alone failed to elicit a CTL response; peptide with another human protein, human albumin, also failed to prime CTL responses. Again, we also failed to obtain priming when animals were injected with 10–1000 fold more peptide in the absence of $\beta_2$-microglobulin.

Experiment C—Peptide titration and analysis of short vs. long peptides

The viral immunogens used in Experiments A and B of this Example correspond to the natural and optimal peptide sequences that bind to class I molecules. It was of interest to determine whether these optimal sequences are required for effective priming. For this purpose, we compared the ability of the short (9 residues, 324–332) and long (16 residues, 321 to 336) forms of the Sendai virus nucleoprotein peptide to prime CTL responses. Experiments were conducted substantially in accordance with Experiment A, except that mice were injected with 290, 97, or 32 ng of Sendai virus nucleoprotein peptide, together with 76 μg of human $\beta_2$-microglobulin in PBS. Spleens were harvested after seven days and restimulated with peptide-pulsed irradiate spleen, as previously described.

As shown in FIGS. 5A and 5B, the both long and short form of the Sendai virus peptide were capable of priming CTL responses in the presence of $\beta_2$-microglobulin, although the short form was definitely more active at the concentrations tested. In all cases, the priming of the CTL response was dependent on the coinjection of $\beta_2$-microglobulin. Higher peptide concentration yielded more efficient priming for both the long and the short forms of the Sendai virus peptide, although efficient priming could also be achieved with smaller amounts of peptides.

EXAMPLE 4

Titration of $\beta_2$-microglobulin Dosage

Individual age and sex matched C57BL/6 mice, once per group, were injected subcutaneously in each flank (two sites per animal) with a total of 290 ng of vesicular stomatitis nucleoprotein virus peptide, with or without 76 µg, 25 µg, 8.3 µg or 2.8 µg of human $\beta_2$-microglobulin (Sigma Chemical Co.) in PBS. After seven days the mice were sacrificed and their spleens removed. Splenocytes were then restimulated with peptide-pulsed irradiated spleen as a source of antigen-bearing antigen-presenting cells in media supplemented with fetal calf serum and rat con A supernatant for five days at 37° C.

After the five days of incubation, the restimulated cells were tested as effectors in a standard $^{51}$Cr release assay. Targets were EL4 cells (no antigen), EL4 cells precultured with 10 µg/ml vesicular virus peptides for 10 hours at 37° C. in media with 10% FCS and then assayed for CTL activity.

As shown in FIG. 6, CTLs were primed in animals that had been injected with the vesicular stomatitis virus peptides together with 76 or 25 µg $\beta_2$-microglobulin, with almost equal efficacy. Priming efficiency dropped off significantly between 25 and 8.3 µg of $\beta_2$-microglobulin.

From the above description, it is apparent that the objects of the present invention have been achieved. While only certain illustrative embodiments have been set forth, alternative embodiments will be apparent from the above description to those skilled in the art.

Having described the invention, what is claimed is:

1. A method of generating a cytotoxic T lymphocyte response to one or more exogenous class I peptides in a mammalian host in vivo comprising the steps of:
   (a) contacting host cells bearing class I MHC molecules with the exogenous class I peptides in the presence of an amount of exogenous free $\beta_2$-microglobulin greater than that normally present in the extracellular fluid of the host and sufficient to promote the association of the exogenous class I peptides with MHC class I molecules on the surface of the host cells to produce sensitized antigen presenting cells; and
   (b) priming a population of the host's T lymphocytes to elicit an antigen-specific MHC-class I restricted cytotoxic T lymphocyte response to the exogenous class I peptides by exposing the population of T lymphocytes to the sensitized antigen-presenting cells.

2. A method according to claim 1, wherein the peptides comprise at least one pathogen-related peptide.

3. A method according to claim 2, wherein the T lymphocytes of the mammalian host are exposed to the pathogen-related peptides and the $\beta_2$-microglobulin by administering the peptides and the $\beta_2$-microglobulin in vivo.

4. A method according to claim 3, wherein the pathogen-related peptides and the $\beta_2$-microglobulin are administered by simultaneous injection.

5. A method according to claim 4, wherein the $\beta_2$-microglobulin is selected from the group consisting of purified human $\beta_2$-microglobulin, purified murine $\beta_2$-microglobulin, purified bovine $\beta_2$-microglobulin, purified equine $\beta_2$-microglobulin and mixtures thereof.

6. A method according to claim 5, wherein the $\beta_2$-microglobulin is purified human $\beta_2$-microglobulin.

7. A method according to claim 1, wherein the class I peptides comprise a mixture of peptide epitopes derived from the antigenic proteins of a pathogenic organism.

8. A method according to claim 1, wherein the step of contacting the host cells bearing class I MHC molecules with the exogenous class I peptides in the presence of free $\beta_2$-microglobulin is carried out ex vivo.

9. A method according to claim 8, wherein the host cells are obtained from the peripheral blood of the mammalian host.

10. A method according to claim 4, wherein the injection is systemic.

11. A method according to claim 4, wherein the injection is local.

12. A method of inducing cytotoxic T lymphocyte response to one or more class I peptides in a mammalian host comprising the step of simultaneously administering the class I peptides and $\beta_2$-microglobulin to the host, wherein after administration the amount of $\beta_2$-microglobulin present in the serum of the mammalian host is greater than that normally present in the serum of a mammal of the same species as the host and sufficient to promote the association of the class I peptides with the MHC class I molecules on the surface of host cells and elicit an MHC class I-restricted cytotoxic T lymphocyte response to the administered peptides.

13. A method according to claim 12, wherein the class I peptides comprise at least one pathogen-related peptide.

14. A method according to claim 12, wherein the $\beta_2$-microglobulin is selected from the group consisting of purified human $\beta_2$-microglobulin, purified murine $\beta_2$-microglobulin, purified bovine $\beta_2$-microglobulin, purified equine $\beta_2$-microglobulin and mixtures thereof.

15. A method according to claim 14, wherein the $\beta_2$-microglobulin is purified human $\beta_2$-microglobulin.

16. A composition capable of promoting the association of one or more exogenous class I peptides with class I MHC molecules on the surface of mammalian host cells, the composition comprising the exogenous class I peptides and free $\beta_2$-microglobulin in an amount sufficient such that, upon administration of the composition to the mammalian host cells, the amount of free exogenous $\beta_2$-microglobulin in the extracellular fluid is raised to an amount greater than that normally present in the extracellular fluid of the mammalian host.

17. The composition according to claim 16, wherein the class I peptides comprise a mixture of peptide epitopes derived from the antigenic proteins of a pathogenic organism.

18. The composition according to claim 17, wherein the class I peptides are recognized by different HLA-types.

19. The composition according to claim 16, wherein the composition promotes the association of exogenous class I peptides with class I MHC molecules on the surface of mammalian host cells when administered ex vivo.

20. The composition according to claim 16, wherein the composition promotes the association of exogenous class I peptides with class I MHC molecules on the surface of mammalian host cells when administered in vivo.

21. The composition according to claim 16, wherein the $\beta_2$-microglobulin is selected from the group consisting of purified human $\beta_2$-microglobulin, purified murine $\beta_2$-microglobulin, purified bovine $\beta_2$-microglobulin, purified equine $\beta_2$-microglobulin and mixtures thereof.

22. The composition according to claim 21, wherein the $\beta_2$-microglobulin is purified human $\beta_2$-microglobulin.

* * * * *